US011752131B2

(12) United States Patent
Taleb et al.

(10) Patent No.: US 11,752,131 B2
(45) Date of Patent: Sep. 12, 2023

(54) METHODS AND PHARMACEUTICAL COMPOSITIONS FOR THE TREATMENT OF OBESITY

(71) Applicants: INSERM (Institut National de la Sante et de la Recherche Medicale), Paris (FR); Universite Paris Descartes, Paris (FR)

(72) Inventors: Fatima-Soraya Taleb, Paris (FR); Ziad Mallat, Paris (FR); Alain Tedgui, Paris (FR)

(73) Assignees: INSERM (INSTITUT NATIONAL DE LA SANTE ET DE LA RECHERCHE MEDICALE), Paris (FR); UNIVERSITE PARIS DESCARTES, Paris (FR)

( * ) Notice: Subject to any disclaimer, the term of this patent is extended or adjusted under 35 U.S.C. 154(b) by 360 days.

(21) Appl. No.: 16/075,204

(22) PCT Filed: Feb. 17, 2017

(86) PCT No.: PCT/EP2017/053597
§ 371 (c)(1),
(2) Date: Aug. 3, 2018

(87) PCT Pub. No.: WO2017/140835
PCT Pub. Date: Aug. 24, 2017

(65) Prior Publication Data
US 2018/0369198 A1  Dec. 27, 2018

(30) Foreign Application Priority Data
Feb. 19, 2016 (EP) .................................... 16305190

(51) Int. Cl.
| | |
|---|---|
| *A61K 31/405* | (2006.01) |
| *A61P 3/04* | (2006.01) |
| *A61P 3/10* | (2006.01) |
| *A61P 9/12* | (2006.01) |
| *A61K 31/196* | (2006.01) |
| *A61K 31/343* | (2006.01) |
| *A61K 31/381* | (2006.01) |

(52) U.S. Cl.
CPC .......... *A61K 31/405* (2013.01); *A61K 31/196* (2013.01); *A61K 31/343* (2013.01); *A61K 31/381* (2013.01); *A61P 3/04* (2018.01); *A61P 3/10* (2018.01); *A61P 9/12* (2018.01)

(58) Field of Classification Search
CPC .. A61K 31/405; A61K 31/196; A61K 31/343; A61K 31/381; A61P 3/04; A61P 3/10
See application file for complete search history.

(56) References Cited

U.S. PATENT DOCUMENTS

2007/0105907 A1* 5/2007 Prendergast .......... C07C 333/22
514/337

FOREIGN PATENT DOCUMENTS

| | | |
|---|---|---|
| ES | 2 446 494 A1 | 3/2014 |
| JP | 2008 074744 A | 4/2008 |
| WO | 2007/075772 A2 | 7/2007 |

OTHER PUBLICATIONS

Shao et al. "Curcumin Prevents High Fat Diet Induced Insulin Resistance and Obesity via Attenuating Lipogenesis in Liver and Inflammatory Pathway in Adipocytes", PLOS One, 2012; 7(1):e28784 (12 pgs). (Year: 2012).*
Jeong et al. "Curcumin Suppresses the Induction of Indoleamine 2,3-Dioxygenase by Blocking the Janus-Activated Kinase-Protein Kinase Cd-STAT1 Signaling Pathway in Interferon-g-Stimulated Murine Dendritic Cells", J Biol Chem; 2009; 284(6):3700-3708. (Year: 2009).*
Weisberg et al. "Dietary Curcumin Significantly Improves Obesity-Associated Inflammation and Diabetes in Mouse Models of Diabesity". Endocrinology, 2008; 149:3549-3558. (Year: 2008).*
Brandacher et al. "Chronic Immune Activation Underlies Morbid Obesity: Is IDO a Key Player?". Current Drug Metabolism. 2007; 8: 289-295. (Year: 2007).*
Qian et al. "Efficacy of Levo-1-Methyl Tryptophan and Dextro-1-Methyl Tryptophan in Reversing Indoleamine-2,3-Dioxygenase-Mediated Arrest of T-Cell Proliferation in Human Epithelial Ovarian Cancer". Cancer Res. 2009; 69(13):5498-5504. (Year: 2009).*
Barnes AS. "The Epidemic of Obesity and Diabetes". Tex Heart Inst J. 2011; 38(2):142-144. (Year: 2011).*
Moon et al. "Serum Tumor Necrosis Factor-Alpha Levels and Components of the Metabolic Syndrome in Obese Adolescents". Metabolism. Jul. 2004; 53(7):863-867. (Year: 2004).*
Legeay et al. Nutrients, 2015, vol. 7, pp. 5443-5468 (Year: 2015).*
Chang et al. Nutrition, 2011, vol. 27, pp. 463-470 (Year: 2011).*
Soliman et al. Oncotarget, 2014, vol. 5, No. 18, pp. 8136-8146 (Year: 2014).*
Vacchelli et al. OncoImmunology, 2014, vol. 3, No. 10, e957994, 10 pages (Year: 2014).*
Ling et al.; "Anti-CD4OL mediated protection from type 1 diabetes in the RIP-GP mouse model is mediated in part through indoleamine 2,3 dioxegenase"; FASEB Journal, vol. 19, No. 4, Suppl. S, Part 1, Mar. 2005, p. A337.

* cited by examiner

*Primary Examiner* — James D. Anderson
(74) *Attorney, Agent, or Firm* — WC&F IP (57) ABSTRACT

The present invention relates to methods and pharmaceutical compositions for the treatment of obesity. In particular, the present invention relates to a method of treating obesity in a subject in need thereof comprising administering to the subject a therapeutically effective amount of an indoleamine 2-3 dioxygenase (IDO) inhibitor.

6 Claims, 9 Drawing Sheets

Figure 4A (first part)

Figure 4A (second part)

METHODS AND PHARMACEUTICAL COMPOSITIONS FOR THE TREATMENT OF OBESITY

FIELD OF THE INVENTION

The present invention relates to methods and pharmaceutical compositions for the treatment of obesity.

BACKGROUND OF THE INVENTION

Obesity is a condition characterized by an excess of body fat. The prevalence of overweight and obesity is considered an important public health issue in the world. Roughly two thirds of US adults meet the criteria for overweight or obesity. Actually, obesity is an important risk factor for coronary heart disease (CHD), ventricular dysfunction, congestive heart failure, stroke, and cardiac arrhythmias. Furthermore obesity is closely associated with type 2 diabetes, metabolic syndrome and hepatic disorders such as non-alcoholic fatty liver disease. Furthermore epidemiologic evidences suggest that obesity increases the risk of cirrhosis. Thus, there is a need for treating obesity and obesity-related disorders, such as NIDDM, metabolic syndrome or non-alcoholic fatty liver disease. Weight loss drugs that are currently used for the treatment of obesity have limited efficacy and significant side effects. However the side effects of current drugs limit their use. For instance dexfenfluramine was withdrawn from the market because of suspected heart valvulopathy.

SUMMARY OF THE INVENTION

The present invention relates to methods and pharmaceutical compositions for the treatment of obesity. In particular, the present invention is defined by the claims.

DETAILED DESCRIPTION OF THE INVENTION

The inventors have demonstrated that indoleamine 2-3 dioxygenase invalidation and inhibition could be suitable for the treatment of obesity and its consequences.

Accordingly a first object of the present invention relates to a method of treating obesity in a subject in need thereof comprising administering to the subject a therapeutically effective amount of an indoleamine 2-3 dioxygenase (IDO) inhibitor.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "obesity" has its general meaning in the art and refers to a condition characterized by an excess of body fat. The operational definition of obesity is based on the Body Mass Index (BMI), which is calculated as body weight per height in meter squared ($kg/m^2$). Obesity refers to a condition whereby an otherwise healthy subject has a BMI greater than or equal to 30 $kg/m^2$, or a condition whereby a subject with at least one co-morbidity has a BMI greater than or equal to 27 $kg/m^2$. An "obese subject" is an otherwise healthy subject with a BMI greater than or equal to 30 $kg/m^2$ or a subject with at least one co-morbidity with a BMI greater than or equal 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$. The increased risks associated with obesity may occur at a lower BMI in people of Asian descent. In Asian and Asian-Pacific countries, including Japan, "obesity" refers to a condition whereby a subject with at least one obesity-induced or obesity-related co-morbidity that requires weight reduction or that would be improved by weight reduction, has a BMI greater than or equal to 25 $kg/m^2$. An "obese subject" in these countries refers to a subject with at least one obesity-induced or obesity-related co-morbidity that requires weight reduction or that would be improved by weight reduction, with a BMI greater than or equal to 25 $kg/m^2$. In these countries, a "subject at risk of obesity" is a person with a BMI of greater than 23 kg/m2 to less than 25 $kg/m^2$.

In particular, the method of the present invention is particularly suitable for controlling weight gain in a subject in need thereof comprising administering to the subject a therapeutically effective amount of a indoleamine 2-3 dioxygenase (IDO) inhibitor. The method of the present invention is also particularly suitable for stimulating weight loss in a subject in need thereof comprising administering to the subject a therapeutically effective amount of a indoleamine 2-3 dioxygenase (IDO) inhibitor.

The method of the present invention is also particularly suitable for the prophylactic treatment of obesity related diseases.

The term "obesity-related diseases" encompasses disorders that are associated with, caused by, or result from obesity. Examples of obesity-related disorders include overeating and bulimia, diabetes, hypertension, elevated plasma insulin concentrations and insulin resistance, dyslipidemia, hyperlipidemia, breast, prostate, endometrial and colon cancer, heart disease, cardiovascular disorders, abnormal heart rhythms and arrhythmias, myocardial infarction, congestive heart failure, coronary heart disease, angina pectoris, cerebral infarction, cerebral thrombosis and transient ischemic attack, and osteoarthritis. Other examples include pathological conditions showing reduced metabolic activity or a decrease in resting energy expenditure as a percentage of total fat-free mass. Further examples of obesity-related disorders include metabolic syndrome, also known as syndrome X, insulin resistance syndrome, type II diabetes, impaired fasting glucose, impaired glucose tolerance, inflammation, such as systemic inflammation of the vasculature, atherosclerosis, hypercholesterolemia, hyperuricaemia, as well as secondary outcomes of obesity such as left ventricular hypertrophy. Obesity-related disorders also include the liver abnormalities associated with obesity such as non-alcoholic fatty liver disease (NAFLD) a rising cause of cirrhosis associated to obesity and metabolic syndrome. Indeed, NAFLD can present as simple steatosis or evolve towards inflammation and steatohepatitis (NASH), with a 20% risk of cirrhosis after 20 years. "Dyslipidemia" is a major risk factor for coronary heart disease (CHD). Low plasma levels of high density lipoprotein (HDL) cholesterol with either normal or elevated levels of low density (LDL) cholesterol is a significant risk factor for developing atherosclerosis and associated coronary artery disease in humans. Dyslipidemia is often associated with obesity.

In particular, the method of the present invention is particularly suitable for improving insulin sensitivity in a subject in need thereof (e.g. an obese) comprising administering to the subject a therapeutically effective amount of an indoleamine 2-3 dioxygenase (IDO) inhibitor.

As used herein, the term "indoleamine 2-3 dioxygenase" or "IDO" has its general meaning in the art and refers to a heme-containing intracellular enzyme that catalyzes the first and rate-determining step in the degradation of the essential amino acid L-tryptophan to N-formyl-kynurenine. N-formyl-kynurenine is then metabolized by multiple steps to eventually produce nicotinamide adenine dinucleotide (NAD+). Thus, the term "IDO inhibitor" refers to any compound that is capable to inhibit IDO expression or activity. As used herein the term 'IDO activity" refers to the production, release, expression, function, action, interaction or regulation of IDO. Any aspect of IDO activity can be evaluated. In particular, the IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity by forming a covalent bond with the enzyme.

IDO inhibitors are well known in the art and are typically described in the following patent applications WO2004094409, WO2007075598, WO2007095050, WO2008036642, WO2008036643, WO2008036652, WO2008036653, WO2008058178, WO2008115804, WO2009073620, WO2009132238, WO2010005958, WO2011045340, WO2011045341, WO2012142237, WO2014081689, WO2014150646, WO2014150677, WO2015002918, WO2015006520, and WO2015031295 and in the following publications: Eduard Dolušić & Raphaël Frédérick Indoleamine 2,3-dioxygenase inhibitors: a patent review (2008-2012) Expert Opinion on Therapeutic Patents Volume 23, Issue 10, October 2013, pages 1367-1381; Tiziana Di Pucchio, Silvio Danese, Raimondo De Cristofaro & Sergio Rutella MD PhD Inhibitors of indoleamine 2,3-dioxygenase: a review of novel patented lead compounds Expert Opinion on Therapeutic Patents Volume 20, Issue 2, February 2010, pages 229-250.

Examples of IDO inhibitors include without limitation 1-methyl-tryptophan (IMT), β-(3-benzofuranyl)-alanine, β-(3-benzo(b)thienyl)-alanine), 6-nitro-tryptophan, 6-fluoro-tryptophan, 4-methyl-tryptophan, 5-methyl tryptophan, 6-methyl-tryptophan, 5-methoxy-tryptophan, 5-hydroxy-tryptophan, indole 3-carbinol, 3,3'-diindolylmethane, epigallocatechin gallate, 5-Br-4-Cl-indoxyl 1,3-diacetate, 9-vinylcarbazole, acemetacin, 5-bromo-tryptophan, 5-bromoindoxyl diacetate, 3-Amino-naphtoic acid, pyrrolidine dithiocarbamate, 4-phenylimidazole a brassinin derivative, a thiohydantoin derivative, a β-carboline derivative or a brassilexin derivative. Preferably the IDO inhibitor is selected from 1-methyl-tryptophan, β-(3-benzofuranyl)-alanine, 6-nitro-L-tryptophan, 3-Amino-naphtoic acid and β-[3-benzo(b)thienyl]-alanine or a derivative or prodrug thereof.

Other examples of IDO inhibitors the following compounds:

Exiguamine A

Tsitsikammamines

In some embodiments, the IDO inhibitor is an inhibitor of IDO expression. An "inhibitor of expression" refers to a natural or synthetic compound that has a biological effect to inhibit the expression of a gene. In a preferred embodiment of the invention, said inhibitor of gene expression is a siRNA, an antisense oligonucleotide or a ribozyme. For example, anti-sense oligonucleotides, including anti-sense RNA molecules and anti-sense DNA molecules, would act to directly block the translation of IDO mRNA by binding thereto and thus preventing protein translation or increasing mRNA degradation, thus decreasing the level of IDO, and thus activity, in a cell. For example, antisense oligonucleotides of at least about 15 bases and complementary to unique regions of the mRNA transcript sequence encoding IDO can be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732). Small inhibitory RNAs (siRNAs) can also function as inhibitors of expression for use in the present invention. IDO gene expression can be reduced by contacting a subject or cell with a small double stranded RNA (dsRNA), or a vector or construct causing the production of a small double stranded RNA, such that IDO gene expression is specifically inhibited (i.e. RNA interference or RNAi). Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and typically cells expressing IDO. Typically, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

By a "therapeutically effective amount" is meant a sufficient amount of the IDO inhibitor of the present invention for reaching a therapeutic effect. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, typically from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

According to the invention, the IDO inhibitor is administered to the subject in the form of a pharmaceutical composition. Typically, the IDO inhibitor may be combined with pharmaceutically acceptable excipients, and optionally sustained-release matrices, such as biodegradable polymers, to form therapeutic compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The IDO inhibitor can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the typical methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents to a small tumor area. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

The invention will be further illustrated by the following figures and examples. However, these examples and figures should not be interpreted in any way as limiting the scope of the present invention.

FIGURES

FIG. 1: Ido1 deficiency leads to a decrease of weight and fat mass. A Weight of Bl6 and IdoKO mice during 20 weeks of NCD or HFD. B fat mass evaluated by MRI in WT and IdoKO mice fed with HFD during 20 wks. C weights of epiWAT, ingWAT, retWAT from b16 (n=10) and idoKO (n=10) mice.

FIG. 2: Ido inhibition or deficiency improves insulin sensibility. A Insulin tolerance test in Bl6 (n=10), L-1MT-treated mice (n=10) and Ido ko mice (n=7) adjusted on the percentage of fat mass gained after 9 wks of HFD and B after 20 wks of HFD for Bl6 and Idoko mice.

FIG. 3: Ido invalidation and inhibition improves insulin sensitivity. A OGTT in b16 (n=10), L-1MT-treated mice (n=10) and Idoko mice (n=7) after 9 wks of HFD B plasma insulin levels during OGTT after 9 wks (B) or 20 wks (E) of HFD. C and F HOMA-IR index normalized to the fat mass of Bl6, L1-MT-treated mice and Idoko mice after 9 wks or 20 wks of HFD.

FIG. 4: Ido invalidation decreases inflammation. A facs analysis in epi and ing WAT from b16 (n=5) and Ido ko (n=5) fed with HFD during 20 wks. B-C cytokine and adiponectin measurements in supernatants of epi and ing WAT explants from b16 (n=10) and Ido ko (n=10) fed with HDF during 20 wks.

EXAMPLE

Material & Methods

Animals

C57BL/6 Ido-1-/- mice were from the Jackson Laboratory. Seven week-old Bl6 and Idoko male mice were subjected to HFD containing 60% fat during 20 weeks.

In Vivo Studies

The oral glucose tolerance test was performed in mice food deprived for overnight prior to an oral administration of 3 g/kg glucose. Blood was sampled from the tail vein at 0, 5, 15, 30, 60 and 120 min in order to assay glucose concentration (glucometer, France). Plasma insulin concentration was measured using ELISA kit (Crystal Chem Inc., Downers Grove, Ill., USA). HOMA-IR in mice was calculated using the equation (fasting glucose concentration× fasting insulin concentration)/405).

Insulin tolerance tests (ITT) was performed in mice food deprived 5 h prior intraperitoneal injection of insulin (0.75 U/kg). Blood was sampled from the tail vein at 0, 5, 15, 30, 60 and 120 min in order to assay glucose concentration (glucometer, France).

Adipose Cell Isolation and Flow Cytometry Analyses

The stromal vascular fraction (SVF) containing mononuclear cells and preadipocytes was extracted from adipose tissue and used for flow cytometry analysis.

Briefly, adipose tissue was digested using collagenase (Roche) to obtain adipocytes and cells of the SVF. After 15 min incubation with Fc block, SVF cells were resuspended in fluorescence-activated cell sorter (FACS) buffer and stained with appropriate antibodies conjugated to fluorochromes for 30 min at 4° C. in the dark: F4/80 PE (eBioscience, #12-4801-82), Cd11b vFluor450 (eBioscience, #48-0112-82), Cd11c PE-Cy7: BD 558079 (BD, #558079), Cd206 AlexaFluor 647 (Biolegend, #141712).

Adipose Tissue Culture

Mouse adipose tissue biopsies (0.1 g) were minced and incubated in 1 ml of endothelial cell basal medium (PromoCell) containing 1% bovine serum albumin, penicillin (100 U/ml), and streptomycin (100 mg/ml). Adipose tissue-conditioned medium (ATCM) were recovered after 24 h and stored at −80° C. until analysis. Cytokine and adiponectin concentrations from ATCM were analysed with ELISA kits (BD and R&D systems).

Results

1/Effect of Ido Invalidation on Body Weight and Fat Mass

Figure 1A:
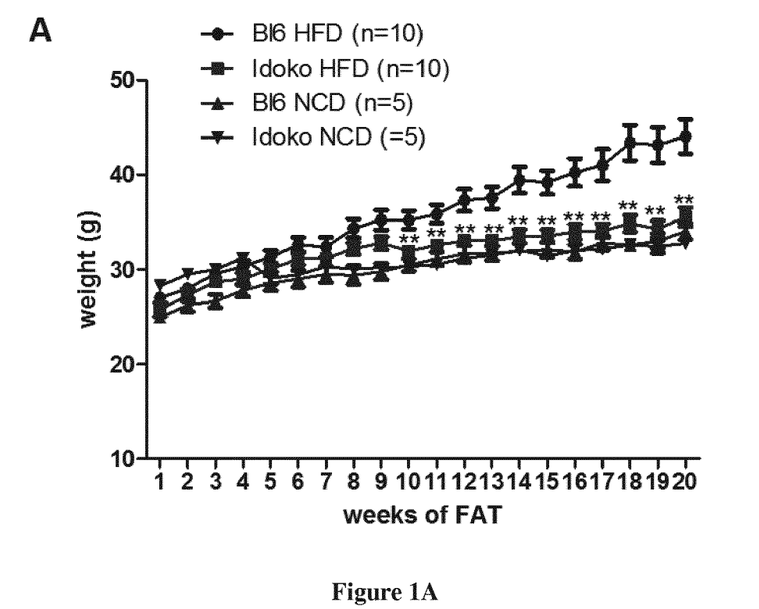
Figure 1B:
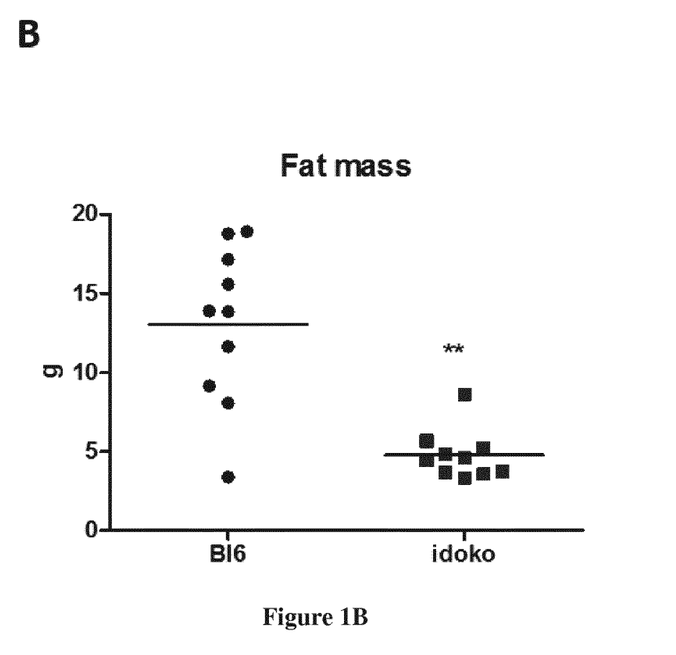

Seven-week-old male C57BL/6 mice genetically ablated for Ido1 (IdoKO) and age- and sex-matched WT (Bl6) were fed with either a normal chow diet (NCD) or a high-fat diet (HFD, 60% FAT) for 20 weeks. We did not observe any differences in weight between NCD-fed Bl6 and IdoKO mice (FIG. 1A). However, contrary to Bl6 mice which gained weight with time, IdoKO mice on the HFD maintained their weight as NCD-fed Bl6 and IdoKO mice groups (FIG. 1A). Evaluation of fat mass with magnetic resonance imaging (MRI) confirmed higher fat mass in Bl6 group in comparison with Idoko mice on HFD (FIG. 1B), without a change in lean mass.

Figure 1C:
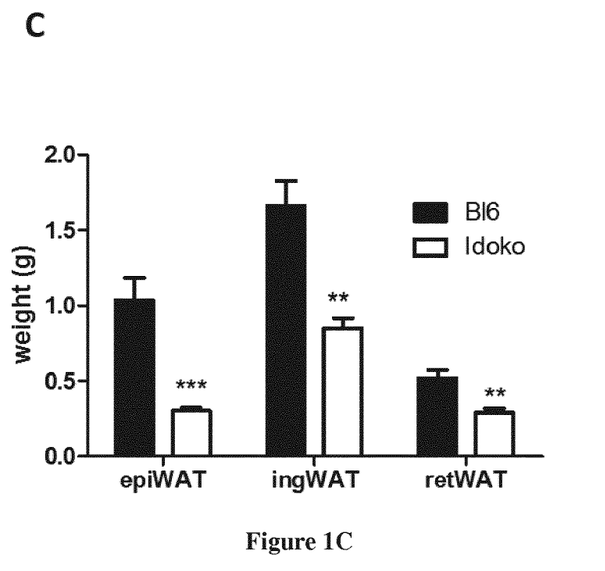

These results were confirmed after sacrifice as assessed by a decrease of weight of both intra-abdominal white adipose tissues (WATs) such as retroperitoneal (ret) and epididymal (epi) fat tissues as well as subcutaneous white adipose tissue (WAT) as inguinal (ing) fat tissue (FIG. 1C).

2/Effect of Ido Invalidation and Inhibition on Insulin Sensitivity

Figure 2A:
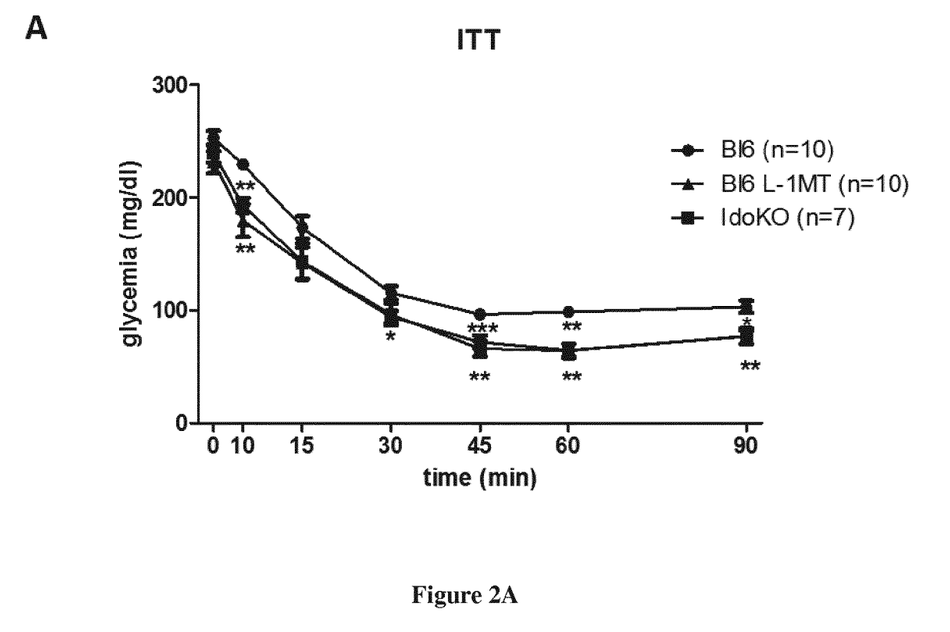
Figure 2B:
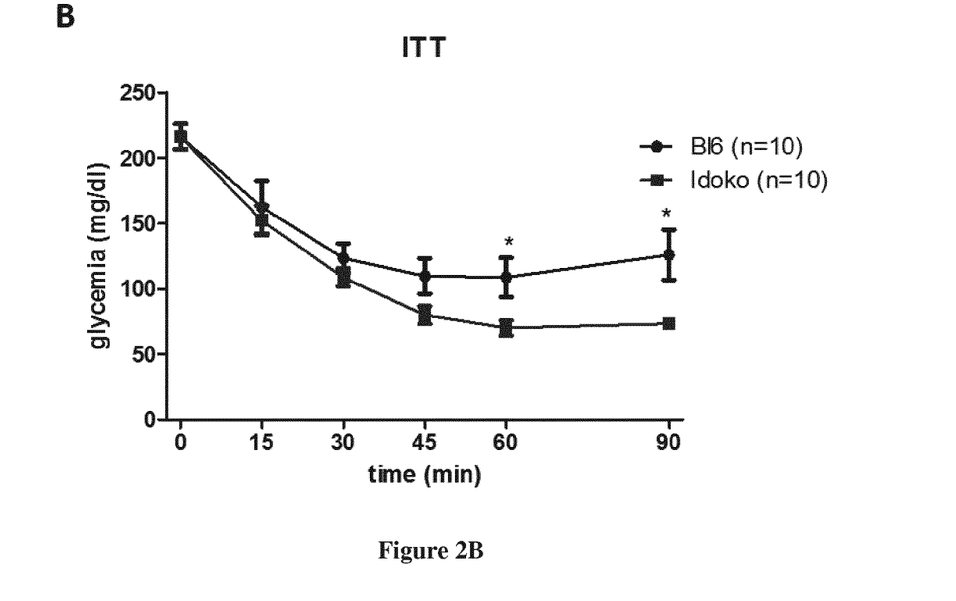
Figure 3A:
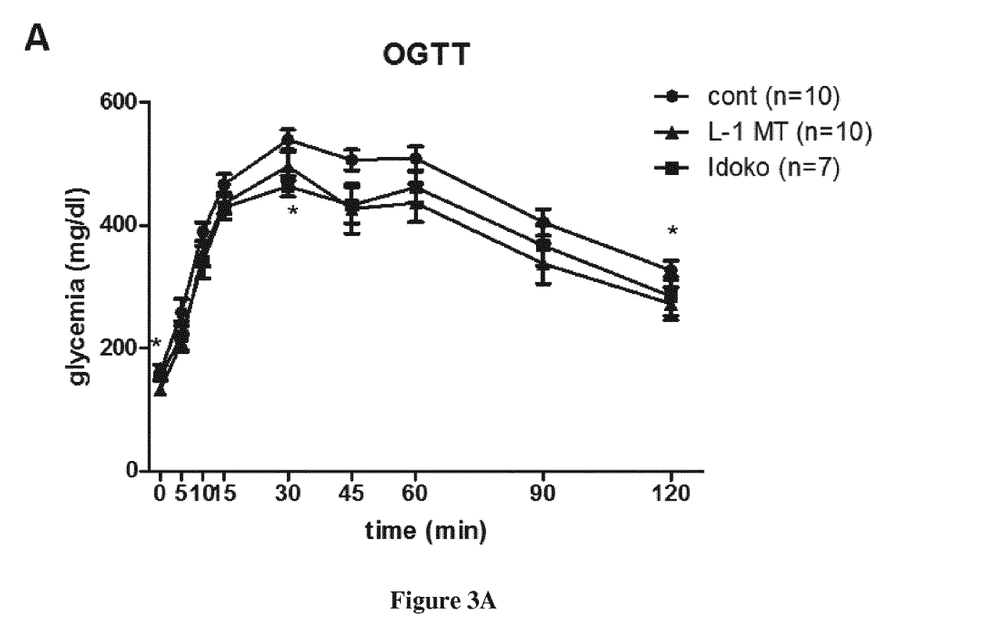
Figure 3B:
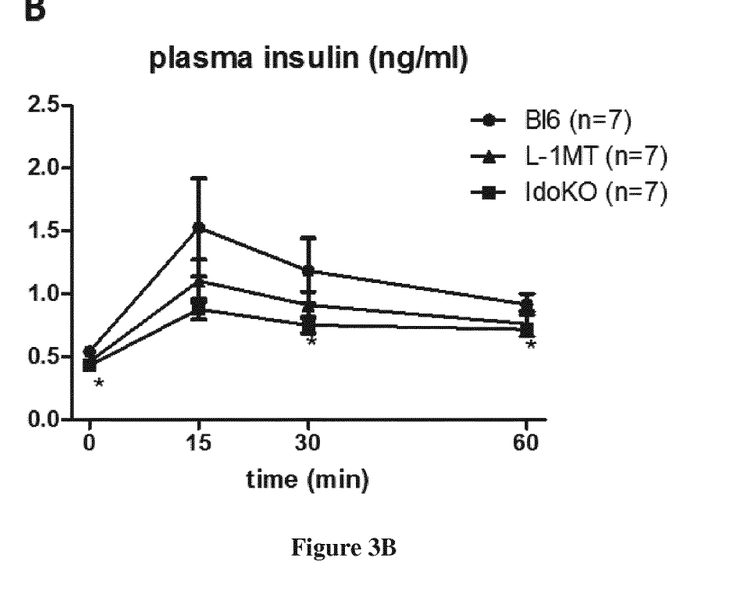
Figure 3C:
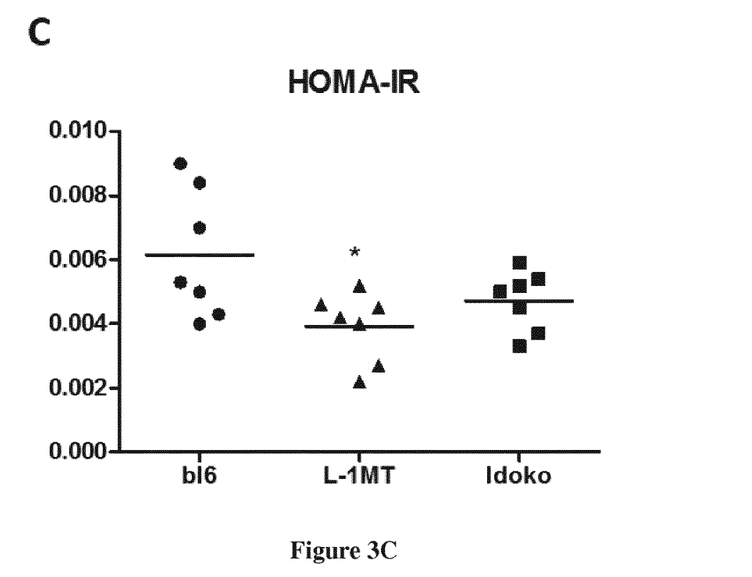
Figure 3D:
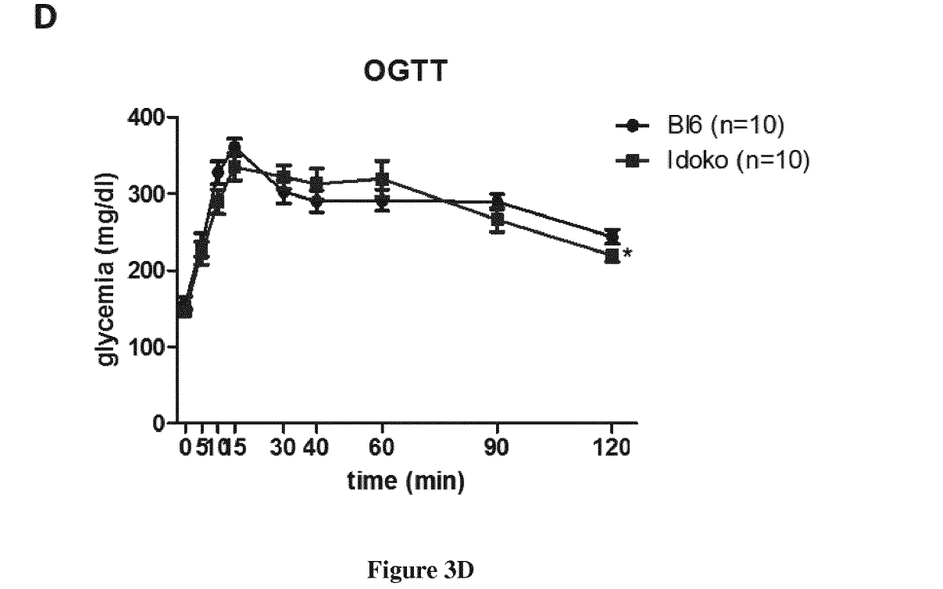
Figure 3E:
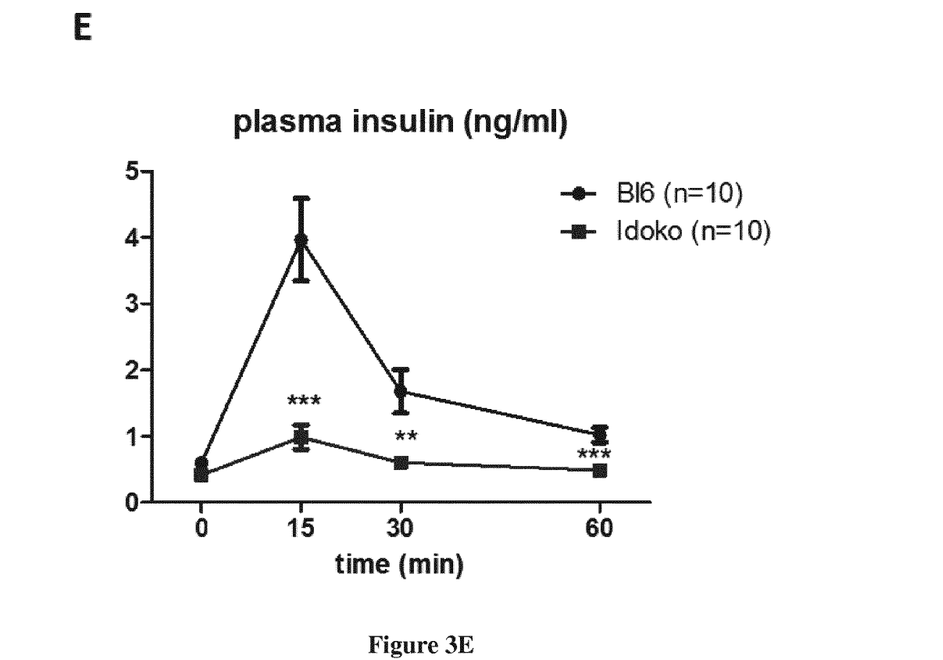
Figure 3F:
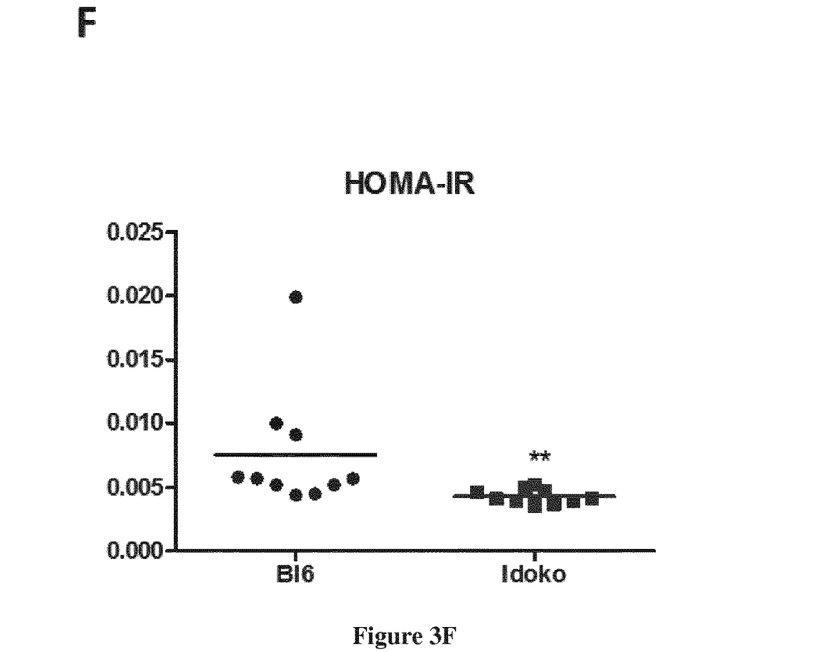

We next examined the effect of Ido deficiency or inhibition on glucose homeostasis in HFD-fed mice. To this end, we performed insulin tolerance tests (ITT) on Bl6, Idoko mice and Ido inhibitor (L-1 methyl tryptophan, L-1MT)-treated mice after 9 wks or 20 wks of HFD. In those settings, the Idoko and L-1MT-treated mice were more insulin sensitive than the Bl6 mice after 9 wks of HFD (FIG. 2A) and 20 wks of FAT diet (FIG. 2B).

Oral glucose tolerance tests (OGTTs) confirmed that, despite similar plasma glucose levels, Idoko have significantly lower plasma insulin levels. Moreover, the insulin resistance index (HOMA-IR) was lower in Ido KO mice or L1MT-treated mice after 9 or 20 wks of HFD (FIG. 3).

3/Effect of Ido Invalidation on Inflammation

Figure 4A:
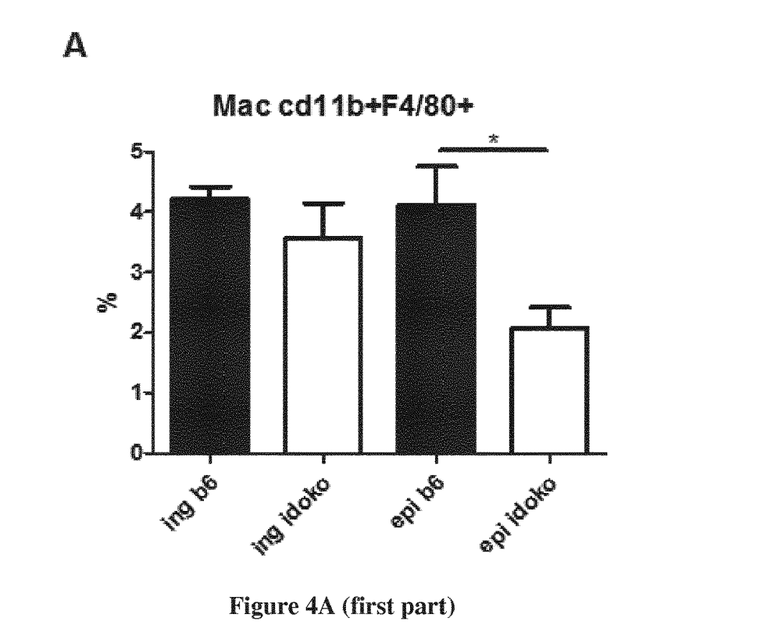
Figure 4B:
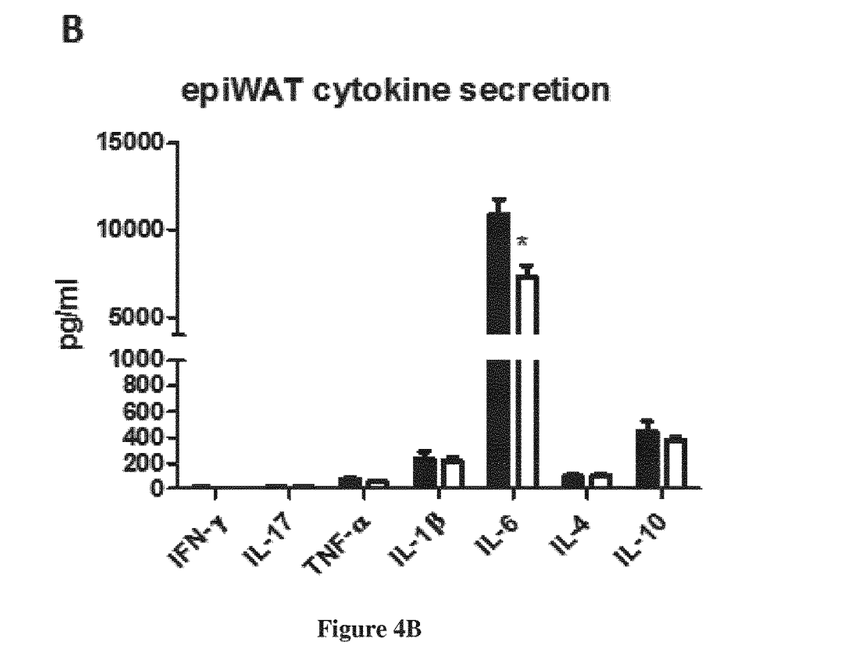
Figure 4C:
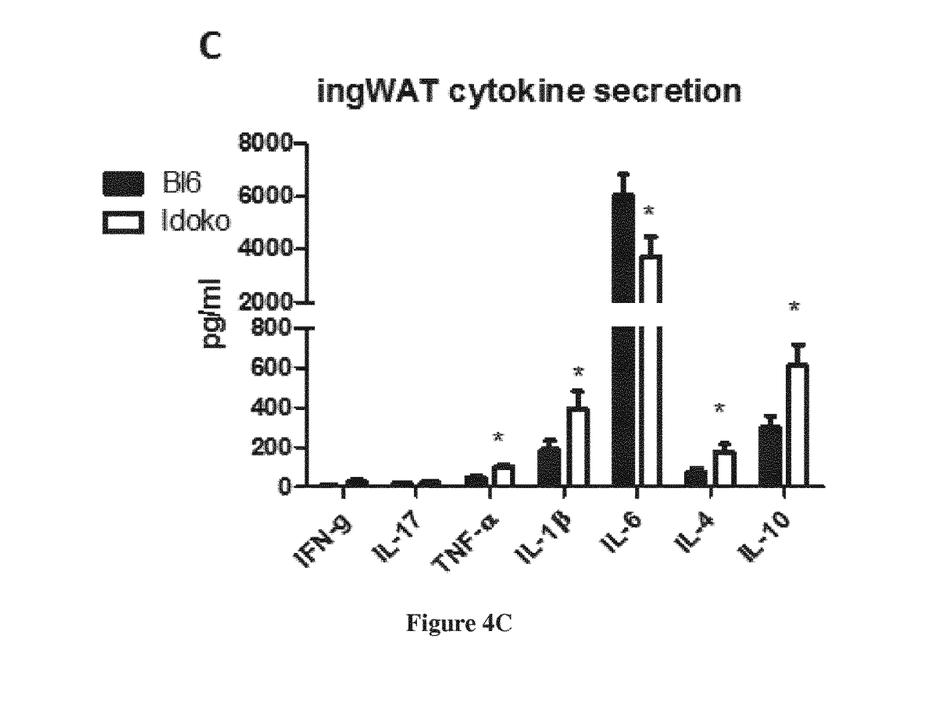
Figure 4D:
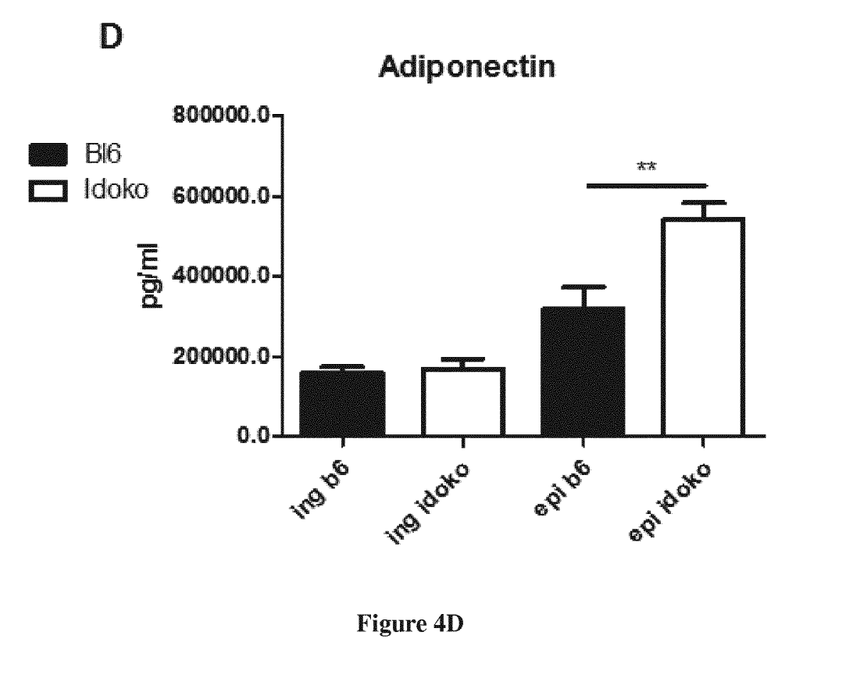

Ido invalidation leads to a significant decrease of macrophages in EpiWAT compared to that in Bl6 controls on the same diet (FIG. 4A). Furthermore, EpiWAT macrophages from IdoKO mice expressed higher levels of the typical M2 surface antigen Cd206 than those from WT controls on the HFD, but expression of the M1 marker Cd11c was unchanged (FIG. 4A), suggesting anti-inflammatory profile in EpiWAT. Similarly, EpiWAT explants from idoKO mice on the HFD produced lower levels of inflammatory factors such as Ifn-g, Il-6, with no difference in Il-1β or Tnf-α, Il-10 and Il-4 production compared to those from WT mice on the same diet (FIG. 4B). IngWAT did not show the same inflammatory properties as EpiWAT in obese IdoKO mice, as compared to HFD-fed WT mice. In particular, we observed no change of macrophage infiltration, no change of macrophage phenotype and increase of some inflammatory factors such as Il-1β or Tnf-α, but a decrease of others such as il-6 and a significant increase of an anti-inflammatory factor, Il-10 (FIG. 4C).

REFERENCES

Throughout this application, various references describe the state of the art to which this invention pertains. The disclosures of these references are hereby incorporated by reference into the present disclosure.

The invention claimed is:

1. A method of treating obesity in an obese subject in need thereof, comprising administering to the obese subject a therapeutically effective amount of an indoleamine 2,3-dioxygenase (IDO) inhibitor selected from the group consisting of β-(3-benzofuranyl)-alanine, β-(3-benzo(b)thienyl)-alanine, 6-nitro-tryptophan, 6-fluoro-tryptophan, 4-methyl-tryptophan, 5-methyl tryptophan, 6-methyl-tryptophan, 5-methoxy-tryptophan, 5-hydroxy-tryptophan, 3,3'-diindolylmethane, 5-Br-4-Cl-indoxyl 1,3-diacetate, 9-vinylcarbazole, acemetacin, 5-bromo-tryptophan, 5-bromoindoxyl diacetate, pyrrolidine dithiocarbamate, and 4-phenylimidazole.

2. A method of treatment to reduce severity of or delay onset of at least one symptom of an obesity-related disease in an obese subject in need thereof, comprising administering to the obese subject a therapeutically effective amount of an indoleamine 2,3-dioxygenase (IDO) inhibitor selected from the group consisting of β-(3-benzofuranyl)-alanine, β-(3-benzo(b)thienyl)-alanine, 6-nitro-tryptophan, 6-fluoro-tryptophan, 4-methyl-tryptophan, 5-methyl tryptophan, 6-methyl-tryptophan, 5-methoxy-tryptophan, 5-hydroxy-tryptophan, 3,3'-diindolylmethane, 5-Br-4-Cl-indoxyl 1,3-diacetate, 9-vinylcarbazole, acemetacin, 5-bromo-tryptophan, 5-bromoindoxyl diacetate, pyrrolidine dithiocarbamate, and 4-phenylimidazole,
    wherein said at least one symptom is selected from the group consisting of impaired fasting glucose, impaired glucose tolerance, inflammation, systemic inflammation, low plasma levels of high density lipoprotein (HDL) cholesterol with either normal or elevated levels of low density (LDL) cholesterol, impaired insulin sensitivity, and reduced metabolic activity or resting energy expenditure as a percentage of total fat-free mass.

3. The method of claim 2, wherein the obesity-related disease is selected from the group consisting of diabetes, hypertension, elevated plasma insulin concentration, insulin resistance, dyslipidemia, and hyperlipidemia.

4. A method of improving insulin sensitivity in an obese subject or a subject at risk of obesity in need thereof, comprising administering to the obese subject a therapeutically effective amount of an indoleamine 2,3-dioxygenase (IDO) inhibitor selected from the group consisting of β-(3-benzofuranyl)-alanine, β-(3-benzo(b)thienyl)-alanine, 6-nitro-tryptophan, 6-fluoro-tryptophan, 4-methyl-tryptophan, 5-methyl tryptophan, 6-methyl-tryptophan, 5-methoxy-tryptophan, 5-hydroxy-tryptophan, 3,3'-diindolylmethane, 5-Br-4-Cl-indoxyl 1,3-diacetate, 9-vinylcarbazole, acemetacin, 5-bromo-tryptophan, 5-bromoindoxyl diacetate, pyrrolidine dithiocarbamate, and 4-phenylimidazole.

5. A method of inhibiting obesity or delaying onset of at least one symptom of an obesity-related disease in a subject at risk of obesity, comprising administering to the subject a therapeutically effective amount of an indoleamine 2,3-dioxygenase (IDO) inhibitor selected from the group consisting of β-(3-benzofuranyl)-alanine, β-(3-benzo(b)thienyl)-alanine, 6-nitro-tryptophan, 6-fluoro-tryptophan, 4-methyl-tryptophan, 5-methyl tryptophan, 6-methyl-tryptophan, 5-methoxy-tryptophan, 5-hydroxy-tryptophan, 3,3'-diindolylmethane, 5-Br-4-Cl-indoxyl 1,3-diacetate, 9-vinylcarbazole, acemetacin, 5-bromo-tryptophan, 5-bromoindoxyl diacetate, pyrrolidine dithiocarbamate, and 4-phenylimidazole, wherein said at least one symptom is selected from the group consisting of impaired fasting glucose, impaired glucose tolerance, inflammation, systemic inflammation, low plasma levels of high density lipoprotein (HDL) cholesterol with either normal or elevated levels of low density (LDL) cholesterol, impaired insulin sensitivity, and reduced metabolic activity or resting energy expenditure as a percentage of total fat-free mass.

6. The method of claim 5, wherein the obesity-related disease is selected from the group consisting of diabetes, hypertension, insulin resistance, dyslipidemia, and hyperlipidemia.

* * * * *